United States Patent
Schuessler

(10) Patent No.: US 9,380,949 B2
(45) Date of Patent: Jul. 5, 2016

(54) MODULAR SENSOR PLATFORM

(71) Applicant: Samsung Electronics, Ltd., Gyeonggi-do (KR)

(72) Inventor: James Schuessler, San Jose, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/101,200

(22) Filed: Dec. 9, 2013

(65) Prior Publication Data
US 2015/0160048 A1   Jun. 11, 2015

(51) Int. Cl.
A61B 5/00   (2006.01)
A61B 5/0205   (2006.01)
A61B 5/0402   (2006.01)
A61B 5/053   (2006.01)
A61B 5/11   (2006.01)

(52) U.S. Cl.
CPC .......... *A61B 5/02055* (2013.01); *A61B 5/0002* (2013.01); *A61B 5/681* (2013.01); *A61B 5/0402* (2013.01); *A61B 5/0533* (2013.01); *A61B 5/0537* (2013.01); *A61B 5/1118* (2013.01); *A61B 5/4806* (2013.01); *A61B 5/7445* (2013.01); *A61B 2560/045* (2013.01); *A61B 2562/0219* (2013.01)

(58) Field of Classification Search
CPC ..... G01D 11/30; G01D 11/245; G04B 47/00; G04B 37/00; A44C 5/00; A61B 5/681
USPC ...................................................... 73/866.5
See application file for complete search history.

(56) References Cited

U.S. PATENT DOCUMENTS

| 6,619,835 | B2 * | 9/2003 | Kita .............................. 368/281 |
| 7,618,260 | B2 * | 11/2009 | Daniel ................ A44C 5/0007 24/311 |
| 8,251,903 | B2 | 8/2012 | LeBoeuf |
| 8,618,930 | B2 | 12/2013 | Papadopoulos |
| 8,647,268 | B2 | 2/2014 | Tran |
| 2009/0018409 | A1 * | 1/2009 | Banet et al. ................... 600/301 |
| 2009/0306485 | A1 | 12/2009 | Bell |
| 2011/0213255 | A1 | 9/2011 | Finburgh |
| 2011/0288382 | A1 | 11/2011 | Finburgh |
| 2012/0071731 | A1 | 3/2012 | Gottesman |
| 2013/0014706 | A1 | 1/2013 | Menkes |
| 2013/0141235 | A1 * | 6/2013 | Utter, II ................... 340/539.12 |

(Continued)

OTHER PUBLICATIONS

"Blocks modular smartwatch: Like Project Ara for your wrist," W.Shanklin, Gizmag, Mar. 6, 2014.

(Continued)

*Primary Examiner* — Lisa Caputo
*Assistant Examiner* — Nathaniel T Woodward
(74) *Attorney, Agent, or Firm* — Convergent Law Group LLP

(57) ABSTRACT

Exemplary embodiments for reconfiguring a storage system comprise a modular sensor platform, comprising: a base module comprising, a display, a processor, a memory and a communication interface; a band removably coupled to the base module such that the band is replaceable with different types of bands; and a sensor module that collects data from a user, the sensor module in communication with the base module and removably coupled to the band such that the sensor module is replaceable with different types of sensor modules, the sensor module further comprising a plurality of sensor units that are removably coupled to the sensor module such that individual sensor units are replaceable with different types of sensor units.

34 Claims, 3 Drawing Sheets

(56) References Cited

U.S. PATENT DOCUMENTS

2013/0165817 A1 6/2013 Horst
2013/0317333 A1 11/2013 Yang

OTHER PUBLICATIONS

"A Survey on Wearable Sensor-Based Systems for Health Monitoring and Prognosis," A. Pantelopoulos and N.G. Bourbakis, IEEE Transactions on Systems, Man and Cybernetics, vol. 40, No. 1, Jan. 2010.

"Multisensor Fusion in Smartphones for Lifestyle Monitoring," R.K. Ganti, S. Srinivasan, and A. Gacic, International Conference on Body Sensor Networks, 2010.

"A 5.2mW Self-Configured Wearable Body Sensor Network Controller and a 12uW Wireless Powered Sensor for a Continuous Health Monitoring System," J.Yoo, L.Yan, S.Lee, Y.Kim, and H-J Yoo, IEEE Journal of Solid-state Circuits, vol. 45, No. 1, Jan. 2010.

* cited by examiner

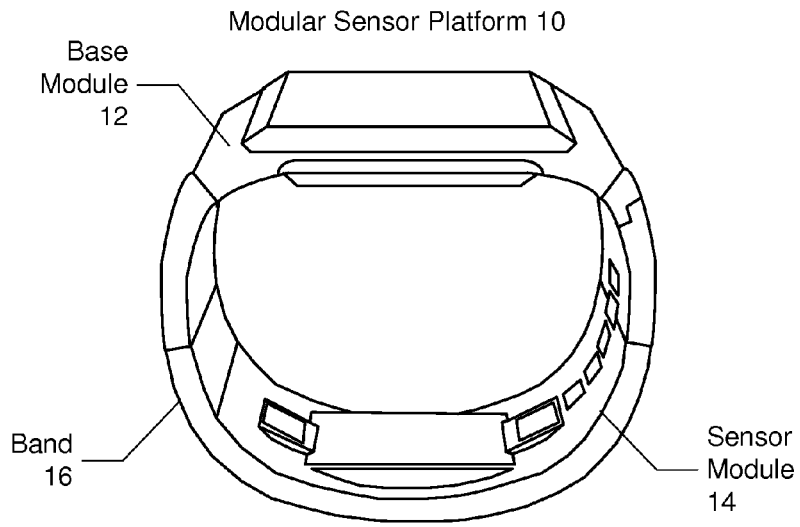
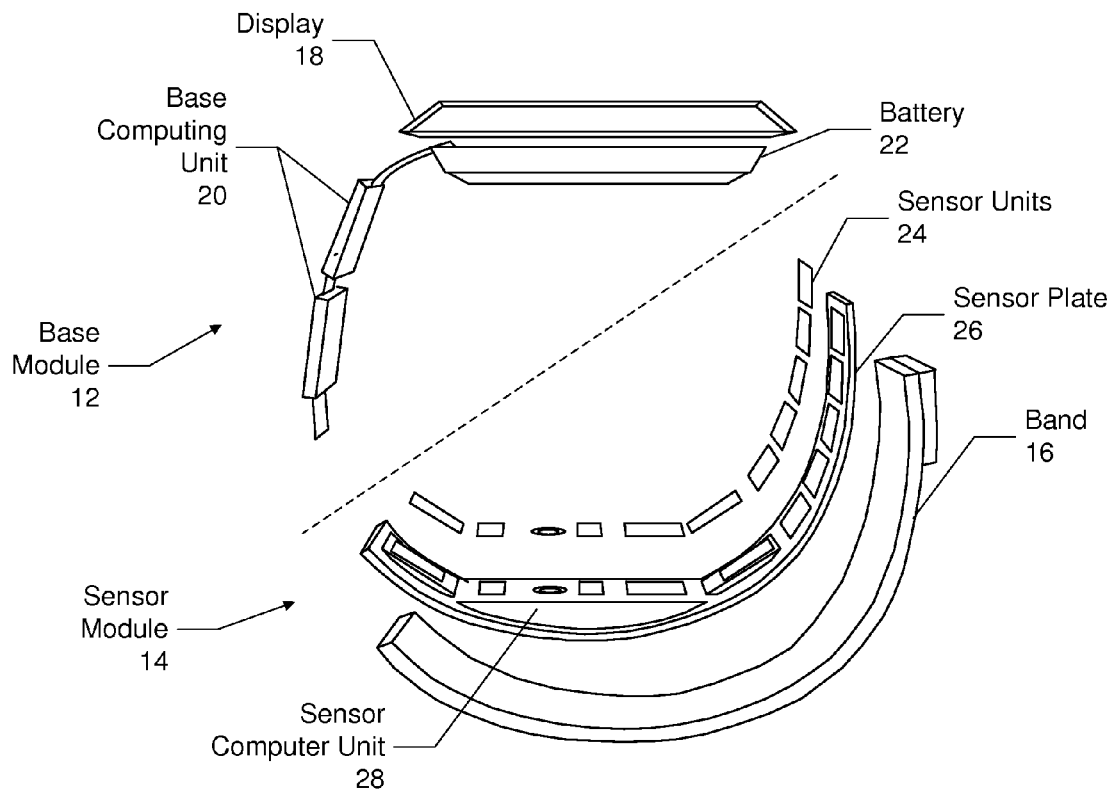

MODULAR SENSOR PLATFORM

BACKGROUND

Wearable devices are becoming increasingly popular. For example, wearable devices equipped with sensors are known that may track user data such as activity data (duration, step count, calories burned), sleep statistics, and/or physiological data (e.g., heart rate, perspiration and skin temperature). Typically, sensor-equipped wearable devices are implemented as bands or watches that may be worn on the user's wrist. However, conventional wearable sensor devices require the user discard or replace the entire device due to a loss of function, even if the loss is caused by a relatively minor component, such as a sensor that becomes worn out due to normal wear. Users also often replace the device when a new device with new or different tracking functions becomes available.

Accordingly, what is needed is an improved architecture for wearable sensor devices that can accommodate both replacement and addition of sensor functionality.

BRIEF SUMMARY

The exemplary embodiment provides a modular sensor platform. Aspects of exemplary embodiment include a base module comprising, a display, a processor, a memory and a communication interface; a band removably coupled to the base module such that the band is replaceable with different types of bands; and a sensor module that collects data from a user, the sensor module in communication with the base module and removably coupled to the band such that the sensor module is replaceable with different types of sensor modules, the sensor module further comprising a plurality of sensor units that are removably coupled to the sensor module such that individual sensor units are replaceable with different types of sensor units.

According to the method and system disclosed herein, the exemplary embodiments provide a platform whereby a plurality of different sensor modules may be sold and manufactured by different entities. These entities may make different types of sensor modules for different use cases. The modular sensor platform of the exemplary embodiments therefore enables different types of base modules, bands, and sensor units to be manufactured and sold separately. The result is that users may be allowed to mix and match different combinations of base modules, sensor modules, bands and sensor units to suit their needs.

BRIEF DESCRIPTION OF SEVERAL VIEWS OF THE DRAWINGS

These and/or other features and utilities of the present general inventive concept will become apparent and more readily appreciated from the following description of the embodiments, taken in conjunction with the accompanying drawings of which:

FIGS. 1A and 1B are block diagrams illustrating exemplary embodiments of a modular sensor platform;

DETAILED DESCRIPTION

Figure 2:
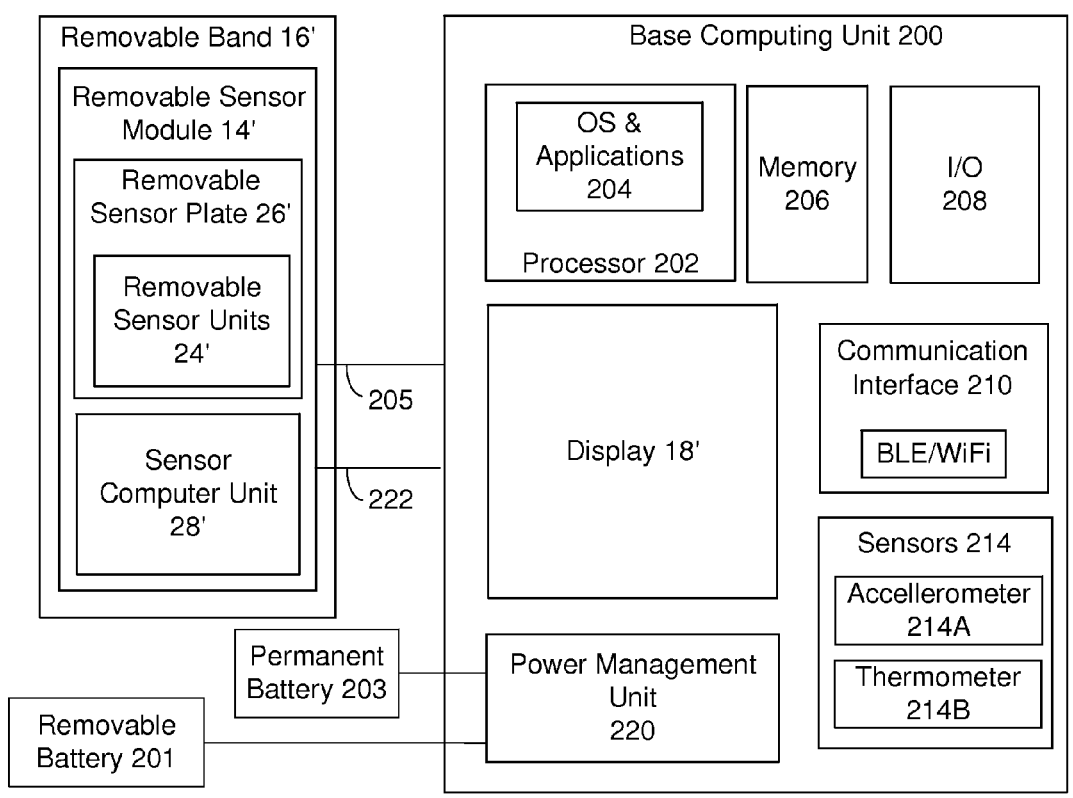
FIG. 2 is a diagram illustrating one embodiment of the modular sensor platform and components comprising the base module.

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures.

Advantages and features of the present invention and methods of accomplishing the same may be understood more readily by reference to the following detailed description of embodiments and the accompanying drawings. The present general inventive concept may, however, be embodied in many different forms and should not be construed as being limited to the embodiments set forth herein. Rather, these embodiments are provided so that this disclosure will be thorough and complete and will fully convey the concept of the general inventive concept to those skilled in the art, and the present general inventive concept will only be defined by the appended claims. In the drawings, the thickness of layers and regions are exaggerated for clarity.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

The term "component" or "module", as used herein, means, but is not limited to, a software or hardware component, such as a field programmable gate array (FPGA) or an application specific integrated circuit (ASIC), which performs certain tasks. A component or module may advantageously be configured to reside in the addressable storage medium and configured to execute on one or more processors. Thus, a component or module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for the components and components or modules may be combined into fewer components and components or modules or further separated into additional components and components or modules.

Unless defined otherwise, all technical and scientific terms used herein have the same meaning as commonly understood by one of ordinary skill in the art to which this invention belongs. It is noted that the use of any and all examples, or exemplary terms provided herein is intended merely to better illuminate the invention and is not a limitation on the scope of the invention unless otherwise specified. Further, unless defined otherwise, all terms defined in generally used dictionaries may not be overly interpreted.

Exemplary embodiments provide a modular sensor platform. Aspects of exemplary embodiment include a base module comprising, a display, a processor, a memory and a communication interface; a band removably coupled to the base module such that the band is replaceable with different types of bands; and a sensor module that collects data from a user. In one embodiment, the sensor module may be removably coupled to the band such that the sensor module is replaceable with different types of sensor modules. In another embodiment, the sensor module comprises a plurality of sensor units that may be removably coupled to the sensor module such that individual sensor units are replaceable with different types of sensor units.

According to the method and system disclosed herein, a modular sensor platform is provided that enables different types of base modules, bands, and sensor units to be manufactured and sold separately by different entities for different use cases. The result is that users may be allowed to mix and match different combinations of base modules, sensor modules, bands and sensor units to suit their needs. Furthermore, developers or researchers in fields related to physiological sensing benefit by focusing development on the sensor itself and utilizing a standard support platform that supplies power, computation and communication in a known configuration.

FIGS. 1A and 1B are block diagrams illustrating exemplary embodiments of a modular sensor platform. The modular sensor platform 10 may include a base module 12, a band 16, and a sensor module 14 coupled to the band 16.

In the embodiment shown in FIG. 1A, the modular sensor platform 10 may be implemented as a wearable sensor device, such as a smart watch that fits on a user's wrist. The sensor module 14 may be positioned within the band 16, such that the sensor module 14 is located at the bottom of the user's wrist in contact with the user's skin to collect physiological data from the user. The base module 12 attaches to the band 16 such that the base module 12 is positioned on top of the wrist and performs functions such as displaying time, performing calculations and displaying data including sensor data collected from the sensor module 14. In one embodiment, the band 16 may be integrated with the base module 14. In another embodiment, the band 16 may be integrated with the sensor module 14. In a further embodiment, the band 16 may be separate from both the base module 12 and the sensor module 14.

In the embodiment shown in FIG. 1B, the base module 12 may comprise a display 18 and a base computing unit 20. As will be discussed more fully with respect to FIG. 2, the base computing unit 20 may include a processor, memory, a communication interface and a set of sensors, such as an accelerometer and thermometer, for instance.

The modular sensor platform 10 enables components of the platform to be easily exchanged with different types of components. For example, in one embodiment, the band 16 may be removably coupled to the base module 12 so that the band 16 is replaceable with a different type of band (e.g., different size, different shape, and/or different materials). Replacement bands may be made by the same or different entities of original band 16. In one embodiment, the band 16 may include a hollow portion for insertion of the base computing unit 20 of the base module 12.

In a further embodiment, the sensor module 14 collects physiological, activity data, and/or sleep statistics from a user and is in communication with the base module 12. The sensor module 14 may be removably coupled to the band 16 such that the sensor module 14 is replaceable with different types of sensor modules.

In one embodiment, the sensor module 14 may further comprise a plurality of sensor units 24 that are removably coupled to the sensor module 14 such that at least a portion of individual sensor units 24 are replaceable with different types of sensor units. In another embodiment, the sensor units 24 may be permanently affixed to the sensor module.

In one embodiment, the sensor units 24 may be housed on a sensor plate 26. According to one embodiment, the sensor plate 26 may be removably coupled to the band 16, such that the sensor plate 26 and all the sensor units 24 thereon may be replaced with a different type of sensor plate 26. For example, the sensor plate 26 may be replaced with a different sized sensor plate 26 to accommodate a different sized wrist. In one embodiment, replacement sensor plates 26 may be provided by the same or a different entity than the original sensor plate 26.

According to one aspect of the exemplary embodiment, at least portion of the sensor units 24 may be further removably coupled to the sensor plate 26 so that the sensor units 24 may be individually replaced with new or different types of sensor units. For example, with electrode-type sensors, the electrodes may wear out over time. Rather than having to buy an entire new smart watch, the user may simply replace worn-out sensor units 24 with new ones by inserting new sensor units 24 into the existing sensor plate 26.

In another embodiment, the sensor plate 26 may be removed from the band 16 so that the existing sensor plate 26 may be used with a different type of band 16. For example, the sensor plate 26 may be removed from a plastic band 16 that is worn during the day and inserted into a felt band that may be worn during sleep. In yet another embodiment, the sensor plate 26 may be removed from the band 16 and replaced with a sensor plate 26 having different types of sensor units 24, including different sized sensor units 24 or sensor units 24 that are spaced differently on the sensor plate 26.

In one embodiment, the sensor plate 26 may be affixed to the band 16 using any number of know mechanisms. For example, in one embodiment, the sensor plate 26 may be affixed to the band 16 via a snap mechanism (e.g., tabs, slots, magnets and the like). In an alternative embodiment, the sensor plate 26 may be affixed to the band 16 via screws.

As shown in FIG. 1B, in one embodiment, the modular sensor platform 10 further includes at least one battery 22. In one embodiment, the battery 22 may be housed within the base module 12. In another embodiment, the battery 22 may be housed within the band 16.

Accordingly, a plurality of different sensor modules may be sold and manufactured by different entities. That is, different entities may make different types of sensor modules for different use cases. The modular sensor platform of the exemplary embodiments therefore enable different types of base modules, bands, sensor plates and sensor units to be manufactured and sold separately. Consequently, a modular sensor platform is provided that enables users to mix and match different combinations of base modules, sensor modules, bands and sensor units to suit their needs.

According to a further aspect of the exemplary embodiment, a user may wear one base module 12 that wirelessly communicates with multiple sensor modules 14 worn on different body parts of the user to form a body area network. Data collected by each of the sensor modules 14 could be bursts to the base module 12 periodically for storage and/or analysis when the base module 12 is in an active mode. Transferring the sensor data only periodically allows the base module 12 to be placed in sleep mode more often to save power. Alternatively, the data could be continually streamed from the sensor modules 14 to the base module 12 if the base module 12 remains in active mode.

FIG. 2 is a diagram illustrating one embodiment of the modular sensor platform and components comprising the base module. In this embodiment, the modular sensor platform 10' may include a removable band 16', and a removable sensor module 14' attached to removable band 16'. The removable sensor module 14' may further include a removable sensor plate 26' attached to the removable band 16', and removable sensor units 24' attached to the removable sensor plate 26'. The removable sensor module 14' may also include a sensor computer unit 28'.

The modular sensor platform 10' further comprises a base computing unit 200, a removable battery 201 and a permanent battery 203. In one embodiment, the base computing unit 200 may communicate with the sensor computer 28' through a communication interface 205. In one embodiment, the communications interface 205 may comprise a serial interface.

The base computing unit 200 may include a processor 202, a memory 206, input/output (I/O) 208, a display 18', a communication interface 210, sensors 214, and a power management unit 220.

The processor 202, the memory 206, the I/O 208, the communication interface 210 and the sensors 214 may be coupled together via a system bus (not shown). The processor 202 may include a single processor having one or more cores, or multiple processors having one or more cores. The processor 202 may execute an operating system (OS) and various applications 204. Examples of the OS may include, but not limited to, Linux and Android™.

The memory 206 may comprise one or more memories comprising different memory types, including DRAM, SRAM, ROM, cache, virtual memory and flash memory, for example. The I/O 208 may comprise a collection of components that input information and output information. Example components comprising the I/O 208 include a microphone and speaker. The communication interface 210 may include a wireless network interface controller (or similar component) for wireless communication over a network. In one embodiment, example types of wireless communication may include Bluetooth Low Energy (BLE) and WLAN (wireless local area network). However, in another embodiment, example types of wireless communication may include a WAN (Wide Area Network) interface, or a cellular network such as 3G, 4G or LTE (Long Term Evolution).

In one embodiment, the display 18' may be integrated with the base computing unit 200, while in another embodiment, the display 18' may be external from the base computing unit 200. The sensors 214 may include any type of microelectromechanical systems (MEMs) sensor, such as an accelerometer/gyroscope 214A and a thermometer 214B, for instance.

The power management unit 220 may be coupled to the removable battery 201 and the permanent battery 203 and may comprise a microcontroller that governs power functions of the base computing unit 200. In one embodiment, the power management unit 220 may also control the supply of battery power to the removable sensor module 14' via power interface 222.

Figure 3:
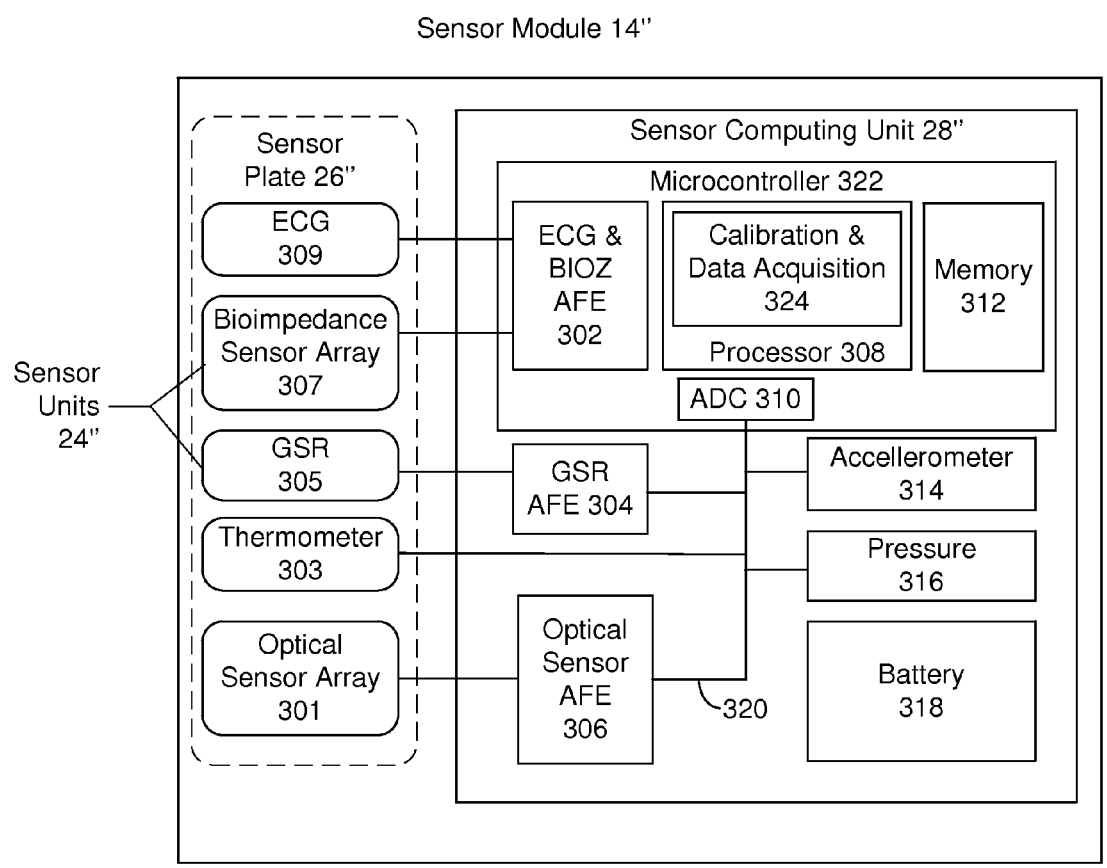
FIG. 3 is a block diagram illustrating components of the sensor module.

FIG. 3 is a block diagram illustrating components of the sensor module. As described above, the sensor module 14" may comprise a plurality of sensor units 24" affixed to a sensor plate 26", and a sensor computing unit 28".

According to one exemplary embodiment, the sensor units 24" may include an optical sensor array 301, a thermometer 303, a galvanic skin response (GSR) sensor array 305, a bioimpedance (BioZ) sensor array 307, and an electrocardiography sensor (ECG) sensor 309, or any combination thereof.

In one embodiment, the optical sensor array 301 may comprise a photoplethysmograph (PPG) sensor array that may measures relative blood flow, pulse and/or blood oxygen level. In one embodiment, the optical sensor array 12 may include an array of discrete optical sensors, where each discrete optical sensor is a combination of at least one photodetector and at least two matching light sources (e.g., LEDs) located adjacent to the photodetector. In this embodiment, the optical sensor array 301 may be arranged on the band so that the optical sensor array 301 straddles a blood vessel, such as the Radial artery or the Ulnar artery.

The thermometer 20 may measure temperature or a temperature gradient. The galvanic skin response (GSR) sensor array 305 may comprise four or more GSR sensors that may measure electrical conductance of the skin that varies with moisture level. The bioimpedance (BioZ) sensor array 307 may comprise four or more bioimpedance sensors that measure bioelectrical impedance or opposition to a flow of electric current through the tissue. In the embodiment shown, the bioimpedance sensor array 16 may be arranged or positioned on the band to straddle a blood vessel, such as the Radial or Ulnar artery. In one embodiment, one or more electrodes comprising the bioimpedance sensors may be multiplexed with one or more of the GSR sensors 305. The electrocardiography sensors (ECG) sensor 309 may measure electrical activity of the user's heart over a period of time.

In one embodiment, the ECG 309, the bioimpedance sensor array 307, the GSR 305, the thermometer 303, and the optical sensor array 201 may be coupled to the sensor computing unit 28" that controls and receives data from the sensor units 24". In one embodiment, the sensor computing unit 28" may be part of the band 16 (not shown). In another embodiment, the sensor computing unit 28" may be part of the sensor plate 26".

In yet another embodiment, a sensor array may be split between fixed and removably attached sensor units, where a portion of the sensor units comprising the sensor array are fixed to the band 16, while another portion are removable attached to the sensor plate 26". For example, the case of an ECG sensor, one electrode may be fixed to the exterior of the band 16, while another electrode is removably attached to the sensor plate 26".

The sensor computing unit 28" may comprise an ECG and bioimpedance (BIOZ) analog front end (AFE) 302, a GSR AFE 304, an optical sensor AFE 306, a processor 308, and analog-to-digital converter (ADC) 310, a memory 312, a three-axis accelerometer 314, a pressure sensor 316 and a battery 318.

As used herein, an AFE may comprise an analog signal conditioning circuitry interface between corresponding sensors and the ADC 310 or the processor 308. The ECG and BIOZ AFE 302 exchange signals with the ECG 18 and the bioimpedance sensor array 16'. The GSR AFE 304 may exchange signals with the GSR sensor array 14. And the optical sensor AFE 306 may exchange signals with the optical sensor array 12. In one embodiment, the GSR AFE 304, the optical sensor AFE 306, the accelerometer 314, and the pressure sensor 316 may be coupled to the ADC 310 via bus 320. The ADC 310 may convert a physical quantity, such as voltage, to a digital number representing amplitude.

In one embodiment, the ECG and BIOZ AFE 302, memory 312, the processor 308 and the ADC 310 may comprise components of a microcontroller 322. The processor 308 in one embodiment may comprise a reduced instruction set computer (RISC), such as a Cortex 32-bit RISC ARM processor core by ARM Holdings, for example.

According to the exemplary embodiment, the processor 308 may execute a calibration and data acquisition component 324 that may perform sensor calibration and data acquisition functions. In one embodiment, the sensor calibration function may comprise a process for self-aligning one more sensor arrays to a blood vessel. In one embodiment, the sensor calibration may be performed at startup, prior to receiving data from the sensors, or at periodic intervals during operation. In one embodiment, during operation the sensor computing unit 28" may collect and store the sensor data in memory 312 for subsequent transfer to the base computing unit 200.

A modular sensor platform has been disclosed. The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor. Accordingly, many modifications may be made by one of ordinary skill in the art without departing from the spirit and scope of the appended claims.

I claim:

1. A modular sensor platform, comprising:
   a base module comprising, a display, a processor, a memory and a communication interface;
   a band coupled to the base module; and
   a sensor module that collects data from a user, the sensor module in communication with the base module and removably coupled to the band such that the sensor module is replaceable with different types of sensor modules, wherein the sensor module further comprises a sensor plate, a plurality of sensor units, and a sensor computer unit coupled to the sensor units, wherein:
      the sensor plate is removably coupled to a side of the band facing the user such that the sensor plate, including all the sensor units and the sensor computer unit thereon, is replaceable with different types of sensor plates; and
      at least a portion of the plurality of sensor units are removably coupled to the sensor plate such that individual sensor units are replaceable with different types of sensor units.

2. The modular sensor platform of claim 1, wherein, the sensor units comprise a two or more combination of: optical sensor array, a thermometer, a galvanic skin response (GSR) sensor array, a bioimpedance (BioZ) sensor array, and an electrocardiography sensor (ECG) sensor.

3. The modular sensor platform of claim 2, wherein the combination of the sensor units includes the optical sensor array, wherein the optical sensor array further comprises: an array of discrete optical sensors, where each discrete optical sensor is a combination of at least one photodetector and at least two matching light sources located adjacent to the photodetector.

4. The modular sensor platform of claim 3, wherein the optical sensor array is arranged on the band so that when the band is worn by a user, the optical sensor array straddles a blood vessel of the user.

5. The modular sensor platform of claim 2, wherein the combination of the sensor units includes the bioimpedance (BioZ) sensor array, wherein the bioimpedance (BioZ) sensor array is arranged on the band so that when the band is worn by the user, the optical sensor array straddles a blood vessel of the user.

6. The modular sensor platform of claim 5, wherein the sensor computer unit further comprises an ECG and bioimpedance (BIOZ) analog front end (AFE), a GSR AFE, an optical sensor AFE, a processor, and analog-to-digital converter (ADC), a memory 312, an accelerometer, a pressure sensor and a battery.

7. The modular sensor platform of claim 6, wherein the processor executes a calibration and data acquisition component that performs sensor calibration and data acquisition functions.

8. The modular sensor platform of claim 1 further comprising a battery.

9. The modular sensor platform of claim 8, wherein the battery comprises a removable battery and a permanent battery.

10. The modular sensor platform of claim 8, wherein the battery is housed within the base module.

11. The modular sensor platform of claim 8, wherein the battery is housed within the band.

12. The modular sensor platform of claim 1, wherein the sensor plate is worn with one type of band during the day and inserted into and worn with a different type during sleep.

13. The modular sensor platform of claim 1, wherein the base module further includes a base computing unit that includes the processor, the memory, the communication interface and a set of sensors, including an accelerometer and thermometer.

14. The modular sensor platform of claim 1, wherein the band is integrated with the base module.

15. The modular sensor platform of claim 1, wherein the band is integrated with the sensor module.

16. The modular sensor platform of claim 1, wherein the base module wirelessly communicates with multiple sensor modules worn on different body parts of the user to form a body area network.

17. A method for providing a modular sensor platform, comprising:
   coupling a base module to a band, wherein the base module comprises, a display, a processor, a memory and a communication interface;
   communicatively coupling a sensor module to the base module, wherein the sensor module comprises a sensor plate, a plurality of sensor units to collect data from a user, and a sensor computer unit coupled to the sensor units;
   removably coupling the sensor plate to a side of the band facing the user such that the sensor module, including all the sensor units and the sensor computer unit thereon, is replaceable with different types of sensor plates; and
   removably coupling at least a portion of the plurality of sensor units to the sensor plate such that individual sensor units are replaceable with different types of sensor units.

18. The method of claim 17, wherein, the sensor units comprise a two or more combination of: optical sensor array, a thermometer, a galvanic skin response (GSR) sensor array, a bioimpedance (BioZ) sensor array, and an electrocardiography sensor (ECG) sensor.

19. The method of claim 18, wherein the combination of the sensor units includes the optical sensor array, wherein the optical sensor array further comprises: wherein the optical sensor array includes an array of discrete optical sensors, where each discrete optical sensor is a combination of at least one photodetector and at least two matching light sources located adjacent to the photodetector.

20. The method of claim 19, wherein the optical sensor array is arranged on the band so that when the band is worn by a user, the optical sensor array straddles a blood vessel of the user.

21. The method of claim 18, wherein the combination of the sensor units includes the bioimpedance (BioZ) sensor array, wherein the bioimpedance (BioZ) sensor array is arranged on the band so that when the band is worn by a user, the optical sensor array straddles a blood vessel of the user.

22. The method of claim 21, wherein the sensor computer unit further comprises an ECG and bioimpedance (BIOZ) analog front end (AFE), a GSR AFE, an optical sensor AFE, a processor, and analog-to-digital converter (ADC), a memory 3212, an accelerometer, a pressure sensor and a battery.

23. The method of claim 22, wherein the processor executes a calibration and data acquisition component that performs sensor calibration and data acquisition functions.

24. The method of claim 17 further comprising a battery.

25. The method of claim 24, wherein the battery comprises a removable battery and a permanent battery.

26. The method of claim 24, wherein the battery is housed within the base module.

27. The method of claim 24, wherein the battery is housed within the band.

28. The method of claim 17, wherein the sensor plate is worn with one type of band during the day and inserted into and worn with a different type during sleep.

29. The method of claim 17, wherein the base module further includes a base computing unit that includes the processor, the memory, the communication interface and a set of sensors, including an accelerometer and thermometer.

30. The method of claim 17, wherein the band is integrated with the base module.

31. The method of claim 17, wherein the band is integrated with the sensor module.

32. The method of claim 17, wherein the base module wirelessly communicates with multiple sensor modules worn on different body parts of the user to form a body area network.

33. A modular sensor platform, comprising:
- a base module comprising, a display, a processor, and a communication interface;
- a band coupled to the base module; and
- a sensor plate including a plurality of sensor units that collect data from a user and a sensor computer unit coupled to the sensor units, wherein:
  - the sensor plate is removably coupled to an exterior surface of the band such that the sensor plate, including all the sensor units and the sensor computer unit thereon, is replaceable with a different size of sensor plate; and
  - at least a portion of the sensor units are removably coupled to the sensor plate such that that individual sensor units are replaceable with different types of sensor units.

34. The modular sensor platform of claim 33, wherein a band is removably coupled to the base module such that the band is replaceable with different types of bands.

* * * * *